United States Patent [19]

Rohowetz

[11] 4,188,437
[45] Feb. 12, 1980

[54] THERMOTROPIC ADHESIVE TAPE

[75] Inventor: Stanley E. Rohowetz, Barrington, Ill.

[73] Assignee: American Can Company, Greenwich, Conn.

[21] Appl. No.: 909,481

[22] Filed: May 25, 1978

[51] Int. Cl.$^2$ .................. B32B 3/14; G01K 11/12
[52] U.S. Cl. ............................................ 428/199; 8/4; 8/25; 73/356; 116/207; 428/209; 428/344; 428/354; 428/913; 428/207
[58] Field of Search ............... 8/1 D, 1 G, 15, 3, 4, 8/25, 26; 23/230 R; 73/356; 116/114 V; 128/2 H; 252/408; 260/38; 350/359; 428/40, 343, 344, 354, 913, 207, 209

[56] References Cited

U.S. PATENT DOCUMENTS

| | | | |
|---|---|---|---|
| 2,798,855 | 7/1957 | Hainsworth | 252/408 |
| 2,798,856 | 7/1957 | Hainsworth | 252/408 |
| 3,078,182 | 2/1963 | Crone et al. | 252/408 |
| 3,288,718 | 11/1966 | Carumpalos | 252/408 |
| 3,311,084 | 3/1967 | Edenbaum | 116/114 V |
| 3,360,337 | 12/1967 | Edenbaum et al. | 106/21 X |
| 3,360,338 | 12/1967 | Edenbaum et al. | 106/19 X |
| 3,360,339 | 12/1967 | Edenbaum et al. | 106/21 X |
| 3,386,807 | 6/1968 | Edenbaum | 73/356 X |
| 3,523,011 | 8/1970 | Bhiwandker et al. | 73/356 X |
| 3,667,916 | 6/1972 | Sliva et al. | 252/408 X |
| 3,704,096 | 11/1972 | Verses et al. | 206/210 X |
| 3,981,683 | 9/1976 | Larsson et al. | 116/114 V X |
| 4,015,937 | 4/1977 | Miyamoto et al. | 252/408 X |
| 4,024,096 | 5/1977 | Wachtel | 260/29.3 |
| 4,045,397 | 8/1977 | Parkinson | 528/130 X |
| 4,070,322 | 1/1978 | Hwang et al. | 260/29.6 M X |

*Primary Examiner*—George F. Lesmes
*Assistant Examiner*—Bruce H. Hess
*Attorney, Agent, or Firm*—Robert P. Auber; Ira S. Dorman; Ernestine C. Bartlett

[57] ABSTRACT

Adhesive tapes which change color in the presence of water or steam at elevated temperature are provided which are useful as sterilization indicators. The tapes comprise an adhesive layer and a polymeric base film containing on one surface thereof a coating of a thermotropic ink comprising a binder resin, a colorant which undergoes a color change in the presence of water or steam at elevated temperature, and a solvent for said binder resin and colorant.

22 Claims, No Drawings

THERMOTROPIC ADHESIVE TAPE

BACKGROUND OF THE INVENTION

1. Prior Art

The prior art appears to be best exemplified by the following patents which were developed in a search:

| | | |
|---|---|---|
| Banczak | 4,021,252 | 5/77 |
| Wachtel | 4,024,096 | 5/77 |
| Parkinson | 4,045,397 | 8/77 |
| Hwang | 4,070,322 | 1/78 |
| Hainsworth | 2,798,855 | 7/57 |
| Hainsworth | 2,798,856 | 7/57 |
| Crone | 3,078,182 | 2/63 |
| Carumpalos | 3,288,718 | 11/66 |
| Edenbaum | 3,311,084 | 3/67 |
| Edenbaum | 3,360,337 | 12/67 |
| Edenbaum | 3,360,339 | 12/67 |
| Edenbaum | 3,360,338 | 12/67 |
| Bhiwandker | 3,523,011 | 8/70 |
| Verses | 3,704,096 | 11/72 |
| Edenbaum | 3,386,807 | 6/68 |
| Chapman | 3,862,824 | 1/75 |

2. Field of the Invention

This invention relates to adhesive tapes bearing on their surfaces ink compositions and particularly jet ink compositions that are particularly useful as sterilization and/or moist thermal exposure indicators.

Indicator tapes of various types are known in the art. For the most part, such materials employ inorganic pigment combinations or must employ a heat-curable agent in the adhesive layer to provide a tape of satisfactory adhesive characteristics during exposure to the elevated temperatures involved in the sterilization techniques. With many of the prior art tapes, manufacture of the tape itself is not without problems since it may be necessary to cure the adhesive during the manufacture of the tape to obtain satisfactoy adhesion properties and it is often difficult to avoid premature color change of the colorants during the heat curing of the heat activatable adhesive. Still other problems are related to the colorants employed, many of which are either too sensitive and activate at too low a temperature or are too insensitive and activate at too high a temperature. Some react to dry heat regardless of the presence of essential moisture thus giving a misleading sterilization indication. Some are unduly photosensitive and deteriorate excessively in the presence of light. Some give only transient or reversible indications or are dependent on the particular substrate on which they are printed and still others are relatively expensive, are not readily printable or impart, prior to sterilization, undesired color to the substrate.

It is an object of this invention to provide indicator tapes which show a distinct difference in color among sterilized and unsterilized packages.

It is another object of this invention to provide a positive and visible indication that packages have been subjected to temperatures at which sterilization or pasteurization of the products contained therein may be achieved.

It is another object of this invention to provide indicator tapes which may comprise a variety of plastic carriers having on their surfaces an ink composition, applied thereto by either conventional coating or by jet printing techniques.

These and other objects of the invention will be apparent from the description of the invention which follows.

SUMMARY OF THE INVENTION

This invention relates to indicator tapes which comprise an adhesive layer and a polymeric or metal base film containing on one surface thereof a coating of a thermotropic ink comprising a binder resin, a least one colorant which undergoes a color change in the presence of water or steam at elevated temperature and a solvent for said binder resin and colorant. More specifically, the preferred tapes comprise a polymeric base layer having on at least one of its surfaces a thermotropic ink comprising a solution compatible resole resin, a colorant either of the type which reacts under the conditions of sterilization or a combination of colorants, one of which is extractible under sterilization conditions; a solvent blend consisting essentially of a lower alcohol or mixture thereof with an oxygenated organic compound including aliphatic or cyclic ketones, esters or ethers, and a surfactant.

The solvent system is so selected as to soften and swell the organic polymeric carrier substrate sufficiently to allow penetration of the colorant ino the body or sub-surface structure thereof, whereby the indicia printed on the substrate become highly resistant to abrasion and to conditions of high temperature and humidity encountered in steam pasteurization and sterilization processes. On the other hand, since the compositions comprise a resole resin exhibiting excellent adhesion to metal or polymeric film, excellent results are also obtained in the absence of the penetration herein described, the penetrating effect of the solvent being a preferred embodiment herein.

The colorant is so selected as to produce a visible color change upon exposure to water or steam at elevated temperature by one of two mechanisms, i.e. through use of a colorant which reacts under process conditions or through use of a combination of dyes comprising an extractible dye.

DETAILED DESCRIPTION OF THE INVENTION

As described herein, the indicator tapes of the invention comprise polymeric or metallic carrier substrates having a coating of a thermotropic ink on its surfaces. The inks contain solvents for the resin and colorant and solvents which temporarily soften and swell the polymeric preferred base carrier sufficiently to allow the colorant component of the ink to penetrate the surface of the polymeric base. Upon removal of the ink solvents by evaporation, the colorant component of the ink remains embedded in the polymeric carrier, primarily within the body or sub-surface rather than on the surface thereof and is substantially immune to abrasion.

For optimum effectiveness in the process of the present invention, it is preferred that there be at least one ink solvent which effects temporary softening and swelling of the polymeric resin base sufficient to allow penetration of the colorant into the swollen body of the carrier. At the same time, the solvent must not dissolve or disrupt the carrier layer, destroy its adhesion to the adhesive layer or in any other way deleteriously affect the protective properties of the carrier.

In the selection of the ink solvents, therefore, consideration must be given to achieving the desired effects on the base layer as well as obtaining the proper solubility for the colorant and other components of the ink and also achieving the desired viscosity and evaporative characteristics, as will be discussed hereinafter.

With regard to the ink solvent effects on the polymeric carrier layer, satisfactory solvents or mixtures of solvents may be selected for use with each of the types of polymeric base carrier layers contemplated for use herein, including epoxy resins, polyvinyl chloride, acrylic resins, polyamide-epoxy resin, polyamides, melamine modified alkyds, etherified melamine formaldehyde-styrene resins and butadiene-styrene copolymers and especially polypropylene and polyethylene terephthalates which are the preferred resins. Ketones, aldehydes and acetals are effective solvents for inks used for printing on carrier layers of the polyvinyl chloride, epoxy, acrylic and styrene-butadiene copolymer types, polypropylene or polyethylene terephthalate. Esters and ethers are also effective with epoxy and acrylic type polymers; dimethyl acetamide, dimethyl formamide and halogenated alcohols are effectively used with polyethylene terephthalates, polyamide and polyamide-epoxy resins, while aromatic organic solvents are satisfactory for inclusion in inks for printing on modified alkyd resins and melamine formaldehyde resins.

Especially preferred as solvents herein are aliphatic ketones, for example 2-butanone, 2-pentanone, 2-hexanone, 2-octanone, 2,4-pentanedione, etc.; cyclic ethers such as furan, dioxane, etc.; aliphatic esters including ethyl acetate, propyl acetate, butyl acetate; aldehydes including dimethyl acetamide, dimethyl formamide, etc. Mixtures of such preferred compounds may also be employed.

As previously mentioned, the inks may be applied to the tapes herein by either contact printing or ink jet printing techniques.

In order to be effective in the formulation of a jet printing ink for polymeric tapes, the solvent medium must readily dissolve sufficient amounts of the dye and any desirable optional components to achieve the desired level of conductivity and visual impact of the ink composition. Further, since some degree of evaporation of solvent will occur in the ink supply and ink return systems, thereby increasing the solids concentration of the composition in these areas, the solvent must have a reserve solvent power sufficient to prevent precipitation in this situation.

Although evaporation of the solvent from the ink supply and return systems is generally undesirable, it is important that the solvent evaporate sufficiently rapidly from the printed image area in order to leave the printed indicia smearproof and moisture proof fairly promptly after the printing operation is carried out. The solvent blend must achieve a satisfactory balance in evaporative properties between these opposed objectives.

In addition to the penetrating solvents discussed above, a primary solvent for the ink components is essential. Such a solvent is one or more of the lower aliphatic alcohols having 1 to 3 carbon atoms, either individually or in blends thereof. Methanol, ethanol, propanol and mixtures thereof are preferred. Additional solvents in which the dye has a high solubility or which aid in penetrating organic coatings on the substrate may also be included. Certain of the relatively low molecular weight glycol ethers such as ethylene glycol monomethyl ether (methyl cellosolve), and ethylene glycol monoethyl ether (ethyl cellosolve) as well as other more polar solvents such as dimethylformamide or dimethyl sulfoxide may also be included. The solvent blend will generally comprise from about 65 to about 97% of the ink composition. The solvent itself may vary from 75% lower alcohol to as little as about 25% alcohol with the remainder of the blend being the penetrating solvents dimethyl formamide, methyl ethyl ketone, etc. as discussed hereinabove.

Mixtures of said alcohol with glycol ethers, dimethyl formamide or ketones are especially preferred. It has been found desirable to include an organic surface active agent in the ink in order to restore and maintain the stability of the ink composition. In this connection, it is most convenient to employ a nonionic surfactant such as fluorinated alkyl esters (commercially available from 3M Co. under the trade names of FC-430, FC-431 and 170, etc.). Such compounds may be present in amounts of about 0.01% to about 0.1% by weight.

Colorants or dyes suitable for use in the ink compositions of this invention are of two types hereafter described as (a) reactive and (b) extractible/non-extractible pairs.

A. Reactive Dyes

Suitable dyes of this type are those which undergo a visible and permanent color change when exposed to temperatures above 215° F. in the presence of steam and which are soluble in the ink solvents and compatible with the components thereof.

A preferred class of dyes are those which may be classified as substituted phenazines and diazotization products thereof derived by diazotization of the reaction product of safranines, e.g. 3,7-diamino-2,8-dimethyl-5-phenyl-phenazinium chloride, with naphthols, phenols, aminobenzenes, etc. Representative dyes may be represented by the formula:

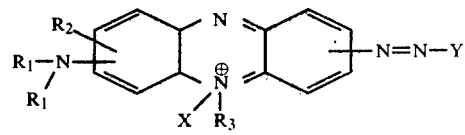

wherein $R_1$ and $R_2$ are lower alkyl radicals or hydrogen, X is an anion, for example, $Cl^-$; $Br^-$,; $R_3$ is an aromatic hydrocarbon radical, for example phenyl, tolyl, xylyl, etc. and Y is an aromatic hydrocarbon radical or substituted aromatic hydrocarbon radical, for example, B-hydroxy-naphthyl, p-dimethyl aminophenyl; p-hydroxy-phenyl; 2-hydroxy-4-ethyl amino-5-methylphenyl; 1,2-dihydroxypropyl-4-aminophenyl, etc.

Exemplary of such dyes are those available commercially as Janus Green B (C.I. Blue 11050); Janus Blue or Indoine Blue (C.I. 12211); Janus Black (C.I. 11825); Copying Black SK (C.I. 11957) and Copying Black 1059/1427 (C.I. 11090).

Although the mechanism by which the reactive dyes undergo a color change is not known with certainty, it is believed that they undergo a chemical reduction of the azo linkage under the conditions of the sterilization of pasteurization resulting in a residual color forming moiety similar to that of Safranine 0(7-diamine-2,8-dimethyl-5-phenyl-phenazinium chloride). Such a reaction may also involve a reduction generated on the metal surface or the formation of metal salts.

It is contemplated that other reactive dyes not specifically enumerated, but of sufficient compatibility, solubility and reactivity under the described conditions to undergo a color change, may also be employed.

In general, the dyes are present in the composition in amounts varying from about 0.1% to about 5% by weight of the composition.

The preferred dyes are the diazo-phenazine class of dyes enumerated above which have been found to exhibit a dark blue color upon application to the substrate and to undergo a color change ranging from pink to red after being subjected to a temperature of at least about 215° F. in the presence of steam for periods of time ranging from about 2 to about 90 minutes. In general, a readily visible color change will be evidenced in as little as 5 minutes depending on the particular temperature. Inks of this type may be employed on the outer surface of the tape or base substrate or they may be applied to the adhesive layer prior to application to the substrate so that they are adjacent the surface of the substrate.

B. Extractible/Non-Extractible Dye Pairs

Suitable dyes of this type are those which function in combination to undergo a visible and permanent color change when exposed to temperatures above about 120° F. in the presence of water or steam. In addition to such color transition characteristics, the dyes must also be soluble in the liquid ink base and be compatible with components thereof. These inks are employed only on the exposed outside surface of the tape.

As contemplated herein, pairs of dyes having differing solubilities or extractability in water are employed. For example, a specific combination may contain a water-extractible blue dye and a relatively non-water-extractible red dye. The extractible blue dye is employed in a weight ratio of at least about 2:1 to the red dye so that markings formed from the composition when applied and dried will be blue. Upon exposure to water at about 120° F. or higher, the blue dye is leached out or extracted and the substrate color thus changes from blue to a permanent and visible red color. The leaching step which is critical to the successful operation of the invention is not observed when water at temperatures below about 120° F. is employed. Additionally, no change in color or leaching takes place when the organic binder resin is fully cured or cross-linked.

Particularly good results have been obtained when using Safranine O as the non-extractible red dye and either of Aniline Blue or Night Green SF as the more soluble leachable blue dyes. Other suitable extractible/non-extractible combinations may be illustrated by Victoria Blue/Palacet Yellow in which a green to blue color change occurs upon extraction of Palacet Yellow. Other suitable combinations may be illustrated by permanent dyes selected from the phenyl safranines, Indamine blue or Rhoduline Violet dyes; extractible dyes from sodium sulfonate salts of triphenylmethane type dyes such as Food Green #1, Acid Blue #7 or from sodium sulfonate salts of Indulines such as Acid Blue #20, Induline ZB, etc.

Preferably, extractible dye pairs are employed which change color at temperatures as slow as about 120° F. although others which change color at somewhat higher temperatures may be employed if desired. The temperature at which the dye becomes extractible is believed to be both a function of its water-solubility as well as of the complexity of the dye molecule and its solubility in the binding resin which may vary depending on the particular dye involved.

It will be obvious that other extractible/non-extractible dye pairs of the same or different color combinations, although not specifically enumerated hereinabove but of sufficient compatibility, solubility, etc. with the components of the ink composition to function as desired, may be employed.

In general, the dyes will be present in the composition in amounts varying from about 0.1% to about 5% by weight of the composition with the soluble dye being present in at least about a 2:1 ratio by weight of the insoluble or non-extractable dye. Alternatively, the dyes may be combined in such proportions that it is unnecessary that one predominate the other in amount. For example, they may blend to form a color which changes upon leaching out the extractible dye. As long as the combination is sufficient to undergo a visible color change, it is suitable for use herein.

The resins preferred for use herein as the binder for the ink components are best classified as phenolic heat-sensitive resins of the resole type. Such resins include those derived from phenol-formaldehyde, resorcinol-formaldehyde, etc. Suitable resole resins for use herein are solution compatible, alcohol soluble cross-linked polymers or prepolymers having molecular weights within the range of about 1,300 to about 10,000. Such resins are alkaline catalyzed phenol-formaldehyde condensation products in which the ratio of formaldehyde to phenol is greater than one and are usually identified as "B-stage" resins which are curable at elevated temperature by further condensation and/or cross-linking through hydroxymethyl groups to insoluble, chemically resistant, adherent polymers. Such resins are well known in the art. Preferred resins for use herein are commercially available under the trade name BLS-2700 or BKS 2600 from Union Carbide Corp. Such alcohol-soluble binders may be employed as such or they may be modified by admixture with other resins including polyvinyl butyral, polyvinyl acetate, polyacrylics, ethylene-acrylic copolymers, polyamides, or other phenolic resins, etc. In general, the binder will be present in the composition in amounts ranging from about 3% to about 30% by weight and preferably from about 5% to about 10% by weight of the ink composition.

The use of resole phenolic resins, described hereinabove, is believed to be critical to the successful utilization of the inks as color-change indicators. It is believed to be essential to the intended result that the resins be such that they are susceptible to further curing after application to the substrate under the same conditions by which the dye component reacts to undergo a color change. Resole phenolic resins as described herein are soluble in the ink solvent, solution compatible with the components of the ink composition and when applied to the substrate undergo further condensation upon subjection to elevated temperature, to produce an adherent, insoluble binder for the ink components. A desirable effect of such binders is to prevent undue dye leaching during the steam process. While the mechanism by which the resin-dye combination functions to convey the desired characteristics to the ink composition is not fully understood, it is believed that the resin cures under the reaction conditions with an accompanying release of water which in turn may serve to accelerate the thermotropic color change of the dye.

If desired, various acidic compounds may be incorporated in the resin component in catalytic amounts to accelerate the resin cure and/or color transition of the composition. Suitable compounds for this purpose include inorganic acids, for example phosphoric acid; esters of such acids, for example dibutyl amino pyrophosphate; organic acids, for example p-toluene sulfonic acid, oxalic acid, etc; metal salts, for example stannous chloride, ferric chloride, etc.

The thermotropic ink compositions may be incorporated into an adhesive tape by providing a polymeric base layer suitably selected from a variety of polymeric substrates including polyvinyl chloride, acrylic resins, polyamide-epoxy resins, polyamides, butadiene-styrene copolymers, polypropylene, polyethylene and polyethylene terephthalates. The adhesive layer of such tapes may be composed of mixed acrylic esters and acids or modified rubber adhesives such as butadiene-styrene copolymers. Coated metal foil such as aluminum foil coated with an adhesive layer may also be used as a base for these thermotropic marking inks. An especially preferred tape for use herein is a polypropylene tape commercially available as "J-Lar II" from Permacel. Suitable tapes of this type may be produced by corona discharge treatment of polypropylene film to increase adhesive sites, priming with an acrylic pimer followed by application of a mixed acrylic ester adhesive layer after which the layer is cured by heating to temperature up to 300° F. preferably in the presence of a peroxide catalyst.

The ink composition may be applied to the tape using either contact printing or ink jet printing. Preferably, a jet ink printing technique is used and the ink is applied to the tape while the tape is on the applicator used to apply the tape to the product. For example, an ink composition of the invention may be applied by contact with a transfer roll or by ink jet apparatus followed by a hot air dry. The coated tape may then be indexed to a cut-off section of the applicator and applied to the product.

The tapes as utilized herein may be affixed to metal or plastic surfaces. While the tapes are designed primarily as sterilization or pasteurization indicators, they may provide other functions as well. For example, the tape may be printed to incorporate a message such as instructions for use or advertising material. It may be used to bond several items together; for example it may be used to fasten an opening key to a metal can, etc.

The following examples will serve to further illustrate the invention.

EXAMPLE 1

A clear biaxially oriented Polypropylene tape, "J-Lar II" (Permacel) comprising a polypropylene base film, an acrylic primer layer and a mixed acrylic ester adhesive layer, was coated on its inside surface by contacting the tape with a transfer roll saturated with the following ink composition:

5% BLS-2700 phenol-formaldehyde resin
1% Indoine Blue Dye
47% Methanol
47% Methyl Cellosolve
0.1% FC-30 fluorinated alkyl ester surfactant The applied ink was air dried on the tape forming blue indicia displaying excellent adhesion to the tape. A length of tape approximately ½" by 1" was cut-off and applied to a printed, filled and sealed metal can which was subjected to sterilization in the presence of steam at about 240° F. for about 75 minutes. After about 10 minutes, a visible change in color of the tape indicia from blue to red was observed.

EXAMPLE 2

A clear polyethylene terephthalate adhesive tape available commercially as "P-922" from Permacel comprising a polyethylene terephthalate base coat with a polyester adhesive layer was coated on its outside surface with the following ink composition:

7% BLS-2700 phenol-formaldehyde resin
0.96% Safranine O
2% Light Green SF
45% Methanol
45% Dimethyl formamide
0.04% FC-430 fluorinated alkyl ester surfactant The ink was dried at 170° F. by subjecting the tape to a hot air blast for 5 seconds. The indicia thus applied were blue in color and exhibited excellent adhesion to the tape.

The printed tape was adhered onto a plastic meat container and the container was processed by immersion in 160° F. water for 4 hours. At the end of 30 minutes, the indicia had changed color from blue to red.

When the above procedure was repeated substituting an aluminum foil adhesive tape comprising aluminum foil base layer with an acrylic adhesive layer, available commercially as "Tape No. 425" or 430" or aluminum foil/silicone adhesive available commercially as "Tape No. 433," all from 3M Company, comparable results were obtained.

Comparable results were also obtained when the ink of this example was applied to the outside surface of an aluminum foil tape having a butadiene-styrene rubber adhesive layer.

It will be seen from the above examples that the invention provides adhesive tapes that are valuable sterilization and/or pasteurization indicators which can provide multiple functions in the packaging industry. Use of the tapes permits the packager to determine upon visual inspection of any given batch of packages that the packages have been exposed to moist temperatures above about 160° F. or 215° F., the specific temperature depending on whether the ink composition becomes activatable at high or low processing temperatures. Provision of both high and low temperature indicators likewise provides versatility permitting use on both metal and plastic containers for a variety of goods. Moreover, the presence of such visible indicia permits the ready rejection of individual containers or packages that have not been processed and traceability of the origin of the package in the event of defects either in the container or its contents. Additionally, the provision of an adhesive tape embodying a thermotropic ink that is applicable to jet ink printing techniques provides for obtaining rapid character changes which further enhances the versatility and use of the invention.

I claim:

1. A thermotropic adhesive tape comprising a base layer of a material selected from the group consisting of polymers and metals, an adhesive coating on one surface of said base layer, and colored markings on either the outer surface of said base layer or the surface of said adhesive layer adjacent said base layer so as to be visible thereon;

said markings being formed from an ink composition comprising a solution of (1) about 3–30% by weight of an alcohol-soluble resole binder resin; (2) about 0.1–5% by weight of a colorant selected from the group consisting of (a) a reactive thermotropic dye capable of exhibiting a visible color change upon exposure to steam at a temperature of at least about 215° F. and (b) a combination of dyes of different color capable of exhibiting a visible color change upon exposure to water or steam at a temperature of at least about 120° F., said dye combination including at least one dye which is water-extractible at said temperature and at least one other dye which is not water-extractible at said temperature; (3) about 65–97% by weight of a solvent blend consisting essentially of (a) about 25–75% of an aliphatic alcohol having 1 to 3 carbon atoms or a mixture thereof and (b) about 25–75% of an organic compound selected from the group consisting of aliphatic and cyclic ketones, aldehydes, acetals, ethers and esters; and (4) about 0.01–0.1% of a surfactant;

said ink composition being disposed on the outer surface of said base layer when said base layer is a metallic material and also being disposed on said base layer when said ink composition comprises said combination of dyes, said ink composition being adhered to said base layer when said base layer comprises a polymeric material by softening and swelling the surfaces of the polymer to allow penetration of the ink; said composition being capable of undergoing a visible and permanent color change as seen on said base layer upon exposure to water at a temperature sufficient to activate a change in color of the colorant.

2. An adhesive tape as claimed in claim 1 in which the base layer is a material selected from the group consisting of polypropylene, polyethylene terephthalate and aluminum foil.

3. An adhesive tape as claimed in claims 1 or 2 in which the resole resin binder is an alkaline catalyzed condensation product of an aromatic compound with formaldehyde in which the ratio of formaldehyde to aromatic compound is greater than 1:1, said aromatic compound being selected from the group consisting of phenol and resorcinol.

4. An adhesive tape as claimed in claim 1 or 2 in which said resole resin has a molecular weight of from about 1,300 to about 10,000.

5. An adhesive tape as claimed in claims 1 or 2 in which the colorant is a reactive thermotropic dye capable of exhibiting a visible color change upon exposure to steam at a temperature of at least about 215° F.

6. An adhesive tape as claimed in claims 1 or 2 in which the colorant is a phenazine dye derived by diazotization of the reaction product of naphthol and 3,7-diamino-2,8-dimethyl-5-phenyl-phenazinium chloride.

7. An adhesive tape as claimed in claims 1 or 2 in which the colorant is Indoine Blue.

8. An adhesive tape as claimed in claims 1 or 2 in which the colorant is a combination of dyes of different colors capable of exhibiting a visible color change upon exposure to water at a temperature of at least about 120° F.

9. An adhesive tape as claimed in claims 1 or 2 in which said extractible dye is Aniline Blue, Palacet Yellow or Light Green SF and said non-extractible dye is Safranine O or Victoria Blue.

10. A thermotropic adhesive tape comprising a base layer of a material selected from the group consisting of polypropylene, polyethylene terephthalate, and aluminum foil, an acrylic polymer adhesive coating on one surface of said base layer and colored markings on either the other surface of said base layer or the surface of said adhesive layer adjacent said base layer so as to be visible thereon;

said markings being formed from an ink composition comprising a solution of (1) about 3 to 7 percent by weight of an alcohol-soluble resole resin derived from an alkaline catalyzed condensation product of an aromatic compound selected from the group consisting of phenol and resorcinol with formaldehyde in which the ratio of formaldehyde to said aromatic compound is greater than 1:1, said resin having a molecular weight within the range of about 1300 L to 10,000; (2) about 1 to 5 percent by weight of a colorant which is a phenazine dye capable of reacting to undergo a visible color change when exposed to steam at a temperature of at least about 215° F.; (3) a solvent consisting essentially of about 25 to 75 percent by weight of an alcohol selected from the group consisting of methanol and ethanol and about about 25 to 75 percent by weight of ethylene glycol monomethyl ether; and (4) about 0.01–0.1 percent by weight of a fluorinated alkyl ester surfactant, said solvent comprising the remainder of said composition;

said ink composition being disposed on the outer surface of said base layer when said base layer is aluminum foil, said ink composition being adhered to said base layer when said base layer comprises one of the polymeric materials by softening and swelling the surfaces of said polymeric material to allow penetration of the ink into the body thereof, and undergoing a visible and permanent color change as seen on said base layer upon exposure to steam at a temperature of at least about 215° F.

11. An adhesive tape as claimed in claim 10 in which said colorant is Indoine Blue.

12. A thermotropic adhesive tape comprising a base layer of a material selected from the group consisting of polypropylene, polyethylene terephthalate, and aluminum foil, an acrylic polymer adhesive coating on one surface of said base layer and colored markings applied to the other surface of said base layer so as to be visible thereon;

said markings being formed from an ink composition comprising a solution of (1) about 3 to 7 percent by weight of an alcohol-soluble resole resin derived from an alkaline catalyzed condensation product of an aromatic compound selected from the group consisting of phenol and resorcinol with formaldehyde in which the ratio of formaldehyde to said aromatic compound is greater than 1:1, said resin having a molecular weight within the range of about 1300 to 10,000; (2) about 1 to 5 percent by weight of a colorant which is a combination of dyes of different color comprising an extractible/non-extractible pair, said combination of dyes being capable of undergoing a visible color change upon exposure to water at a temperature of at least about 120° F.; (3) a solvent consisting essentially of about 25 to 75 percent by weight of an alcohol selected from the group consisting of methanol and ethanol and about 25 to 75 percent by weight of dimethyl formamide; and (4) about 0.01–0.1 percent by weight of a fluorinated alkyl ester surfactant, said solvent comprising the remainder of said composition, said dye pair including one dye which is not water-extractible at said temperature; and one dye which is water extractible at said temperature;

said ink composition being disposed on the outer surface of said base layer and adhered to said base layer when said base layer comprises one of the polymeric materials by softening and swelling the surfaces of the polymer to allow penetration of the ink into the body thereof and undergoing a visible and permanent color change by extraction of the extractible dye from said base layer upon exposure to water at a temperature of at least about 120° F.

13. An adhesive tape as claimed in claim 12 in which the extractible dye is Aniline Blue, Palacet Yellow or Light Green SF and said non-extractible dye is Safranine O or Victoria Blue.

14. A thermotropic adhesive tape comprising a base layer of a material selected from the group consisting of polypropylene and polyethylene terephthalate, an acrylic ester polymer adhesive layer on one surface of said base layer and colored markings on either the other surface of said base layer or the surface of said adhesive layer adjacent said base layer, said markings being formed from an ink composition comprising a solution of about 5% by weight of alcohol-soluble phenol-formaldehyde resole resin, about 1% by weight Indoine Blue dye, about 47% by weight methanol, about 47% by weight methyl cellosolve and about 0.1% by weight fluorinated alkyl ester surfactant, said composition being capable of undergoing a visible and permanent color change upon exposure to steam at a temperature of at least about 215° F.

15. A thermotropic adhesive tape comprising an aluminum foil base layer, an acrylic ester adhesive layer on one surface of said base layer and colored markings on either the other surface of said base layer or the surface of said adhesive layer adjacent said base layer, said markings being formed from an ink composition comprising a solution of about 5% by weight of an alcohol-soluble phenol-formaldehyde resole resin, about 1% by weight Indoine Blue dye, about 47% by weight methanol, about 47% by weight methyl cellosolve and about 0.1% by weight fluorinated alkyl ester surfactant, said composition being capable of undergoing a visible and permanent color change upon exposure to steam at a temperature of at least about 215° F.

16. A thermotropic adhesive tape comprising a base layer of a material selected from the group consisting of polypropylene, polyethylene terephthalate, and aluminum foil, an acrylic ester adhesive layer on one surface of said base layer and colored markings on the other surface of said base layer, said markings being formed from an ink composition comprising a solution of about 7% by weight of an alcohol-soluble phenol-formaldehyde resole resin, about 1% by weight of a mixture of Safranine O and Light Green SF in a weight ratio of about 1:2, about 45% by weight methanol, about 45% by weight dimethyl formamide and about 0.04% by weight fluorinated alkyl ester surfactant, said composition being capable of undergoing a visible and permanent color change upon exposure to water at a temperature of at least about 120° F.

17. A thermotropic adhesive tape comprising an aluminum foil base layer, an acrylic ester adhesive layer on one surface thereof and colored markings on the other surface of said base layer, said markings being formed from an ink composition comprising a solution of about 7% by weight phenol-formaldehyde resole resin, about 1% by weight of a mixture of Safranine O and Light Green SF in a weight ratio of about 1:2, about 45% by weight methanol, about 45% by weight dimethyl formamide and about 0.04% by weight fluorinated alkyl ester surfactant, said composition being capable of undergoing a visible and permanent color change upon exposure to water at a temperature of at least about 120° F.

18. A thermotropic adhesive tape comprising a base layer of a material selected from the group consisting of polymers and metals, an adhesive coating on one surface of said base layer, and colored markings on either the outer surface of said base layer or the surface of said adhesive layer adjacent said base layer so as to be visible thereon;

said markings being formed from an ink composition comprising a solution of (1) about 3–30% by weight of an alcohol-soluble resole binder resin; (2) about 0.1–5% by weight of a colorant selected from the group consisting of (a) a reactive thermotropic dye capable of exhibiting a visible color change upon exposure to steam at a temperature of at least about 215° F. and (b) a combination of dyes of different color capable of exhibiting a visible color change upon exposure to water or steam at a temperature of at least about 120° F., said dye combination including at least one dye which is water-extractible at said temperature and at least one other dye which is not water-extractible at said temperature; and (3) about 65–97% by weight of a solvent blend consisting essentially of (a) about 25–75% of an aliphatic alcohol having 1 to 3 carbon atoms or a mixture thereof and (b) about 25–75% of an organic compound selected from the group consisting of aliphatic and cyclic ketones, aldehydes, acetals, ethers and esters;

said ink composition being disposed on the outer surface of said base layer when said base layer is a metallic material and also being disposed on said base layer when said ink composition comprises said combination of dyes, said ink composition being adhered to said base layer when said base layer comprises a polymeric material by softening and swelling the surfaces of the polymer to allow penetration of the ink; said composition being capable of undergoing a visible and permanent color change as seen on said base layer upon exposure to water at a temperature sufficient to activate a change in color of the colorant.

19. An adhesive tape as claimed in claim 18 in which the base layer is a material selected from the group consisting of polypropylene, polyethylene terephthalate and aluminum foil.

20. An adhesive tape as claimed in claims 18 or 19 in which the resole resin binder is an alkaline catalyzed condensation product of an aromatic compound with formaldehyde in which the ratio of formaldehyde to aromatic compound is greater than 1:1, said aromatic compound being selected from the group consisting of phenol and resorcinol.

21. An adhesive tape as claimed in claims 18 or 19 in which the colorant is a reactive thermotropic dye capable of exhibiting a visible color change upon exposure to steam at a temperature of at least about 215° F.

22. An adhesive tape as claimed in claims 18 or 19 in which the colorant is a combination of dyes of different colors capable of exhibiting a visible color change upon exposure to water at a temperature of at least about 120° F.

* * * * *